US008936925B2

(12) United States Patent
Wang et al.

(10) Patent No.: US 8,936,925 B2
(45) Date of Patent: Jan. 20, 2015

(54) RECONSTITUTION OF 5-ENOLPYRUVYLSHIKIMATE-3-PHOSPHATE SYNTHASE ACTIVITY BY FRAGMENT COMPLEMENTATION

(75) Inventors: Yiping Wang, Beijing (CN); Yicheng Sun, Beijing (CN); Yan Li, Beijing (CN)

(73) Assignee: Peking University, Beijing (CN)

( * ) Notice: Subject to any disclaimer, the term of this patent is extended or adjusted under 35 U.S.C. 154(b) by 1998 days.

(21) Appl. No.: 11/721,856

(22) PCT Filed: Dec. 16, 2005

(86) PCT No.: PCT/CN2005/002219
§ 371 (c)(1),
(2), (4) Date: Dec. 4, 2008

(87) PCT Pub. No.: WO2006/063533
PCT Pub. Date: Jun. 22, 2006

(65) Prior Publication Data
US 2009/0155879 A1    Jun. 18, 2009

(30) Foreign Application Priority Data
Dec. 16, 2004    (CN) .......................... 2004 1 0102289

(51) Int. Cl.
*C12N 9/10*         (2006.01)
*C12N 15/82*        (2006.01)
(52) U.S. Cl.
CPC .......... *C12N 15/8216* (2013.01); *C12N 9/1092* (2013.01); *C12N 15/8257* (2013.01); *C12N 15/8275* (2013.01)
USPC ....................................................... 435/193
(58) Field of Classification Search
None
See application file for complete search history.

(56) References Cited

FOREIGN PATENT DOCUMENTS

WO    WO 00/71701     11/2000
WO    WO 2004/046359   6/2004
WO    WO 2004/046360   6/2004

OTHER PUBLICATIONS

Anderson et al., "'Kinetic Competence' of the 5-Enolpyruvoylshikimate-3-phosphate Synthase Tetrahedral Intermediate," The Journal of Biochemistry, vol. 265, No. 10, pp. 5567-5572 (1990).
Braun et al., "In Vivo Reconstitution of the FhuA Transport Protein of *Escherichia coil* K-12." Journal of Bacteriology, vol. 185, No. 18, pp. 5508-5518 (2003).
Chen et al., "Herbicide resistance from a divided EPSPS protein: the split *Synechocystis* DnaE intcin as an in vivo affinity domain," Gene, vol. 263, pp. 39-48 (2001).
Chin et al., "Protein trans-splicing in transgenic plant chloroplast: Reconstruction of herbicide resistance from split genes," PNAS, vol. 100, pp. 4510-4515 (2003).
Comai et al., "Chloroplast transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," The Journal of Biological Chemistry, vol. 263, No. 29, pp. 15104-15109 (1988).
Daniell et al, "Containment of herbicide resistance through genetic engineering of the chloroplast genome," Nature Biotechnology, vol. 16, pp. 345-348 (1998).
Della-Cioppa et al., "Targeting a Herbicide-Resistant Enzyme for *Escherichia coli* to Chloroplasts of Higher Plants," Biotechnology, vol. 5, pp. 579-584 (1987).
Eschenburg et al., "A New View of the Mechanisms of UDP-*N*-Acetylglucosamine Enolpyruvyl Transferase (MurA) and 5-Enolpyruvylshikimate-3-phosphate Synthase (AroA) Derived from X-ray Structures of Their Tetrahedral Reaction Intermediate States." The Journal of Biological Chemistry, vol. 278, No. 49, pp. 49215-49222 (2003).
Eschenburg et al., "Comparative X-Ray Analysis of the Un-Liganded Fosfomyein-Target MurA," Proteins: Structure, Function, and Genetics, vol. 40, pp. 290-298 (2000).
Hakansson et al., "Protein Reconstitution and 3D Domain Swapping," Current Protein and Peptide Science, vol. 3, pp. 629-642 (2002).
Hollander-Czytko et al., "5-Enolpyruvylshikimate 3-Phosphate Synthase, the Target Enzyme of the Herbicide Glyphosate, Is Synthesized as a Precursor in a Higher Plant," Plant Physiol. vol. 83, pp. 229-231 (1987).
Huynh et al., "5-Enolpyruvyl Shikimate 3-Phosphate Synthase from *Escherichia coli*," The Journal of Biological Chemistry, vol. 263, No. 2, pp. 735-739 (1988).
Huynh et al., "Site-directed Mutagenesis of *Petunia* hybrida 5-Enolpyruvylshikimate-3-phosphate Synthase: Lys-23 Is Essential for Substrate Binding," The Journal of Biological Chemistry, vol. 263, No. 24, pp. 11636-11639 (1988).
McDowell et al., "Characterization of the Complex of a Trifluoromethyl-Substituted Shikimate-Based Bisubstrate Inhibitor and 5-Enolpyruvylshikimate-3-phosphate Synthase by REDOR NMR," Biochemistry, vol. 43, pp. 6606-6611 (2004).

(Continued)

*Primary Examiner* — Rebecca Prouty
(74) *Attorney, Agent, or Firm* — RatnerPrestia

(57) ABSTRACT

The present invention relates to protein fragments of 5-enolpyruvylshikimate-3-phosphate synthase, which are selected from the protein fragment pairs of EPSPS, two such protein fragments can make up full length EPSPS and reconstitute EPSPS activities by complementation without help of any joint structure. The present invention also relates to nucleic acid molecules encoding the protein fragments, expression vectors and cells comprising such nucleic acid molecules. The present invention also relates to methods for reconstituting EPSPS activities by using the fragments or the nucleic acid molecules or the expression vectors of the present invention, as well as methods for dividing the protein fragments of the present invention.

1 Claim, 7 Drawing Sheets

(56) References Cited

OTHER PUBLICATIONS

McDowell et al., "Rotational-echo double-resonance NMR-restrained model of the ternary complex of 5-enolpyruvylshikimate-3-phosphate synthase," Journal of Biomolecular NMR, vol. 28, pp. 11-29 (2004).

Mizyed et al., "Identification of the Catalytic Residues of AroA (*Enol*pyruvylshikimate 3-Phosphate Synthase) Using Partitioning Analysis," Biochemistry, vol. 42, pp. 6986-6995 (2003).

Nelson et al., "Complete genome sequence and comparative analysis of the metabolically versatile *Pseudomonas plaida* KT2440," Environmental Microbiology, vol. 4, No. 12, pp. 799-808 (2002).

Padgette et al., "Arginine Chemical Modification of *Petunia hybrida* 5-*enol*-Pyruvylshikimate-3-phosphate Synthase," Archives of Biochemistry and Biophysics, vol. 266, No. 1, pp. 254-262 (1988).

Padgette et al., "Identification of the Reactive Cysteines of *Escherichia coli* 5-Enolpyruvylshikimate-3-phosphate Synthase and Their Nonessentiality for Enzymatic Catalysis," The Journal of Biological Chemistry, vol. 263, No. 4, pp. 1798-1802 (1988).

Reinbothe et al., "Cytosolic and plastid forms of 5-enolpyruvylshikimate-3-phosphate synthase in *Euglena gracilis* are differentially expressed during light-induced chloroplast development," Mol Gen Genet, vol. 245, pp. 616-622 (1994).

Reinbothe et al., "Overproduction by gene amplification of the multifunctional arom protein confers glyphosate tolerance to a plastid-free mutant of *Euglena gracilis*," Mol Gen Genet, vol. 239, pp. 416-424 (1993).

Schonbrunn et al., "Interaction of the herbicide glyphosate with its target enzyme 5-enolpyruvylshikimate 3-phosphate synthase in atomic detail," PNAS, vol. 98, pp. 1376-1380 (2001).

Schonbrunn et al., "Role of the Loop Containing Residue 115 in the Induced-Fit Mechanism of the Bacterial Cell Wall Biosynthetic Enzyme MurA," Biochemisty, vol. 39, pp. 2164-2173 (2000).

Schonbrunn et al., "Structural basis for the interaction of the fluorescence probe 8-anilino-1-naphthalene sulfonate (ANS) with the antibiotic target MurA," PNAS, vol. 97, pp. 6345-6349 (2000).

Shiba et al., "Functional Assembly of a Randomly Cleaved Protein," PNAS, vol. 89, pp. 1880-1884 (1992).

Shiba et al., "Tripartite Functional Assembly of a Large Class 1 Aminoacyl tRNA Synthetase," The Journal of Biological Chemistry, vol. 267, No. 32, 22703-22706 (1992).

Shuttleworth et al., "Site-Directed Mutagenesis and NMR Studies of Histidine-385 Mutants of 5- Enolpyruvylshikimate-3-phosphate Synthase," Biochemistry, vol. 33. pp. 7062-7068 (1994).

Shuttleworth et al., "Site-Directed Mutagenesis of Putative Active Site Residues of 5-Enolpyruvylshikimate-3-phosphate Synthase," Biochemistry, vol. 38, pp. 296-302 (1999).

Shuttleworth et al., "The H385N Mutant of 5-Enolpyruvylshikimate-3-phosphate Synthase: Kinetics, Fluorescence, and Nuclear Magnetic Resonance Studies," Archives of Biochemistry and Biophysics, vol. 334, No. 1, pp. 37-42 (1996).

Smart et al., "Ultrastructural localization by protein A-gold inununocytochemistry of 5-enolpyruvylshikimic acid 3-phosphate synthase in a plant cell culture which overproduces the enzyme," Planta, vol. 170, pp. 1-6 (1987).

Stallings et al., "Structure and Topological Symmetry of the Glyphosate Target 5-Enolpyruvylshikimate-3-Phosphate Synthase: A Distinctive Protein Fold," PNAS, vol. 88, pp. 5046-5050 (1991).

Stauffer et al., "Chemical shift mapping of shikimate-3-phosphate binding to the isolated N-terminal domain of 5-enolpyruvylshikimate-3-phosphate synthase," FEBS Letters, vol. 499, pp. 182-186 (2001).

Stauffer et al., "Shikimate-3-phosphate Binds to the Isolated N-Terminal Domain of 5-Enolypyruvylshikimate-3-phosphate Synthase," Biochemistry, vol. 40, pp. 3951-3957 (2001).

Watrud et al., "From the Cover: Evidence for landscape-level, pollen-mediated gene flow from genetically modified creeping bentgrass with CP4 EPSPS as a marker," PNAS, vol. 101, pp. 14533-14538 (2004).

Ye et al., "Plastid-expressed 5-enolpyruvylshikimate-3-phosphate synthase genes provide high level glyphosate tolerance in tobacco," The Plant Journal, vol. 25. No. 3, pp. 261-270 (2001).

Barry et al., "Inhibitors of Amino Acid Biosynthesis: Strategies for Imparting Glyphosate Tolerance to Crop Plants," Biosynthesis and Molecular Regulation of Amino Acids in Plants, American Society of Plant Physiologists, pp. 139-145 (Jan. 1, 1992).

Sun et al., "Reconstitution of the enzyme AroA and its glyphosphate tolerance by fragment complementation," FEBS Letters 580:1521-1527 (2006).

US 8,936,925 B2

RECONSTITUTION OF 5-ENOLPYRUVYLSHIKIMATE-3-PHOSPHATE SYNTHASE ACTIVITY BY FRAGMENT COMPLEMENTATION

TECHNICAL FIELD

The present invention relates to a method for reconstitution of 5-enolpyruvylshikimate-3-phosphate synthase (EPSPS) activity by using fragment complementation. More particularly, the present invention relates to the reconstitution of the *Escherichia coli* EPSPS and the glyphosate-tolerant EPSPS mutants, as well as the reconstitution of *Pseudomonas putida* glyphosate-tolerant EPSPS.

TECHNICAL BACKGROUND

Along with the large scale planting of the transgenic plants, increasing attentions have been paid to the biological confinement of transgenic plants. It was observed that a gene encoding glyphosate-tolerant CP4 EPSPS could spread to crops 20 kilometers away from the transgenic plants, even into weeds, by Wruad et al. Proc Natl Acad Sci USA 2004, 101, (40), 14533-8. Thus it is very important to perform biological confinement towards transgenic plants for preventing superweeds and the like.

Modes of exogenous gene spreading of transgenic plants comprise principally the following: diffusion of the pollen from transgenic plants; transgenic plants acting as the recipients of pollen from wild sibling species to form hybrids; gene spreading which may be caused by the DNA of transgenic plants. Recently there are some methods which control the exogenous gene spreading of transgenic plants, e.g., (1) physical isolation, mainly distant isolation, so that the exogenous gene spreading by pollen is blocked; (2) genetic control, including: (a) male sterility; (b) genome incompatibility, that is, a specific exogenous gene is integrated into the crop genome which is incompatible with weeds; (c) maternal inheritance, which has achieved primary success in tobacco (Daniell et al., *Nat Biotechnol* 1998, 16, (4), 345-8), where exogenous genes are introduced into the chloroplasts of plants and subjected to maternal inheritance, thus no spreading into other species by diffusing pollen; (d) seed sterility; (e) transgenic mitigation (TM), where TM genes which are closely linked with target genes, advantageous or neutral to transgenic plants and disadvantageous to the growth of weeds (such as to prevent seeds from spilling out and to reduce the secondary dormancy of seeds) are used to prevent the production of superweeds.

A novel method for controlling the transgene flow of glyphosate-tolerant gene was reported by Ye, G. N. et al. *Plant J* 2001, 25, (3), 261-70 and Chin, H. G. et al. *Proc Natl Acad Sci USA* 2003, 100, (8), 4510-5. In this method, a EPSPS gene was divided into two fragments which were then linked respectively with a gene expressing DanE intein and were co-expressed. A full length EPSPS was formed by self splicing of intein. The resulting *E. coli* or tobacco becomes tolerant to glyphosate. However, the intein-encoding gene itself was introduced into transgenic plants in this method, which might also lead to additional risks such as transgene flow.

Protein fragments derived from proteolytic cleavage or gene expression reconstitute in vivo or in vitro into a complex with the same function as the intact protein. This is known as protein fragment complementation or protein reconstitution technology (e.g., Hakansson, M. et al. *Curr Protein Pept Sci* 2002, 3, (6), 629-42; Braun, M. et al. *J Bacteriol* 2003, 185, (18), 5508-18). It is indicated by a research on fragment complementation of aminoacyl tRNA synthetase that most divisional sites of protein fragment for fragment complementation locate in non-conserved regions. That a protein can be reconstituted means the non-covalent interaction within this protein is quite specific, which makes the protein segments advantageous in forming a natural structure (Shiba, K. et al. *Proc Natl Acad Sci USA* 1992, 89, (5), 1880-4; Shiba, K. et al. *J Biol Chem* 1992, 267, (32), 22703-6). Furthermore, functional reconstitution of a protein means that the protein keeps a relative stable structure, even if the covalent bond is broken. Various non-covalent interactions (such as hydrogen bond, salt bridge and hydrophobic interactions) exist between two peptides for fragment complementation and the interactions are important for retaining stable structure of the protein (Nelson, K. E. et al., Complete genome sequence and comparative analysis of the metabolically versatile *Pseudomonas putida* KT2440. *Environ Microbiol* 2002, 4, (12), 799-808).

We reconstituted active EPSPS in vivo and in vitro by such protein reconstitution. Glyphosate-tolerant EPSPS could also be reconstituted in this way. Fragment complementation of EPSPS can be used in transgenic plants to improve safety and reduce the possibility of superweed formation.

SUMMARY OF THE INVENTION

The present invention relates to 5-enolpyruvylshikimate-3-phosphate synthase (EPSPS) protein fragments, which are fragments selected from EPSPS fragment pairs. The pairs are comprised of two fragments that can connect to form full length EPSPS and reconstitute EPSPS activity by complementation without any joint structure. Preferably, EPSPS fragment pairs are derived from division of EPSPS within a joining region between folding units, between an α-helix and β-sheet, or between two β-sheets, or within a β-sheet or a α-helix. More preferably, they are derived from division of EPSPS within a joining region between folding units, e.g., in the joining regions between folding units 1 and 6, 2 and 6, 3 and 4, 4 and 5, and 3 and 5. More preferably, they are derived from division of EPSPS within one of the folding units 1, 2, 3, 4 or 5. For example, they are divided in the joining region between two β-sheets of folding unit 3, in the α-helix of folding unit 4, in the β-sheet of folding unit 2, between the α-helix and β-sheet of folding unit 1, in the joining region between the α-helix and β-sheet of folding unit 5, or in the joining region between two β-sheets of folding unit 5, or in the β-sheets of folding unit 5.

In the embodiments of the present invention, the EPSPS is wild type EPSPS or its active variants obtained by adding, deleting and/or replacing one or more amino acid residues. Preferably, the EPSPS is the wild type EPSPS of *E. coli* (its full length amino acid sequence and nucleotide sequence are known in the art and are shown in the Sequence Listing) or its glyphosate-tolerant EPSPS active variant. Preferably, the EPSPS is the glyphosate-tolerant EPSPS of *Pseudomonas putida*, such as of *P. putida* CGMCC 0739 (see Chinese Patent Application No. 02117991.3; its full length amino acid sequence and nucleotide sequence are shown in SEQ ID NO: 2 of the present application).

More specifically, the protein fragments of the present invention are preferably fragments from EPSPS, fragment pairs of *E. coli* or of *P. putida* CGMCC 0739, wherein the fragment pairs of *E. coli* are selected from a group consisting of N67/C68, N85/C86, N104/C105, N154/C155, N182/C183, N184/C185, N218/C219, N224/C225, N227/C228, N259/C260, N298/C299, N371/C372, N376/C377, and N383/C384, (As used herein, the fragment pair N67/C68 is comprised of the N-terminal fragment N67 and the C-terminal fragment C68, wherein the N-terminal fragment N67 refers to the fragment from the N-terminus to the residue at position 67 in the EPSPS sequence, and the C-terminal fragment C68 refers to the fragment from the C-terminus to the residue at position 68 in the EPSPS sequence. This nomenclature applies to other fragment pairs), and the fragment pairs of P. putida CGMCC 0739 are selected from a group consisting of N208/C209, N214/C215, N219/C220, N222/C223, and N224/C225. (As used herein, the fragment pair N208/C209 is comprised of the N-terminal fragment N208 and the C-terminal fragment C209, wherein the N-terminal fragment N208 refers to the fragment from the N-terminus to the residue at position 208 in the EPSPS sequence, and the C-terminal fragment C209 refers to the fragment from the C-terminus to the residue at position 209 in the EPSPS sequence. This nomenclature applies to other fragment pairs).

The present invention further relates to a nucleic acid molecule encoding a protein fragment of the present invention, an expression vector carrying the nucleic acid molecule and a cell comprising the nucleic acid molecule or the expression vector. Preferably the cell is a plant cell. The present invention also relates to a transgenic plant comprising the nucleic acid molecule or the expression vector of the present invention or seeds thereof.

The present invention further relates to a method to reconstitute EPSPS, which includes reconstitution of EPSPS activity by using protein fragments or nucleic acid molecules or expression vectors of the present invention with no help of any joining structure.

The present invention further relates to a method of dividing EPSPS or its nucleic acid molecule without any joining structure to obtain the protein fragment or the nucleic acid molecule of the present invention. The EPSPS is divided within a joining region between folding units, between α-helix and a β-sheet, or between two β-sheets, or it is divided within a β-sheet or α-helix. More preferably, it is divided within a joining region between folding units, e.g., in the joining region between folding units 1 and 6, 2 and 6, 3 and 4, 4 and 5, and 3 and 5. More preferably, it is divided within one of the folding units 1, 2, 3, 4 or 5. For example, it is divided in the joining region between two β-sheets of folding unit 3, in the α-helix of folding unit 4, in the β-sheet of folding unit 2, between the α-helix and β-sheet of folding unit 1, in the joining region between the α-helix and β-sheet of folding unit 5, or in the joining region between two β-sheets of folding unit 5, or in the β-sheets of folding unit 5. Even more preferably, the EPSPS is divided in a region selected from a group consisting of: the positions 67-68, 85-86, 104-105, 154-155, 182-183, 184-185, 218-219, N224-C225, N227-C228, 259-260, 298-299, 371-372, 376-377, or 383-384 in the EPSPS of E. coli, or the positions 208-209, 214-215, 219-220, 222-223, or 224-225 in the glyphosate-tolerant EPSPS of P. putida CGMCC 0739.

The present invention also relates to use of an EPSPS fragment or a method of reconstituting EPSPS activity or a method of dividing EPSPS according to the prevent invention in controlling the safety of transgenic plants.

DISCLOSURE OF THE INVENTION

Based on the structure of EPSPS, divisional sites are selected in the regions which might not influence the enzyme activity of EPSPS. Expression vectors are also constituted to express the divided EPSPS fragments. These fragments are then proved to be effective in complementing EPSPS activity in E. coli. Accordingly, the EPSPS fragments and the method for reconstitution of EPSPS as described herein could be used for the application in the field of biological confinement.

EPSPS and its Structure 5-enolpyruvylshikimate-3-phosphate synthase (EPSPS) is a key enzyme involved in aromatic amino acid biosynthesis-shikimic acid biosynthesis pathway in algae, higher plants, bacteria, fungi and apicomplexans of parasites. It catalyzes the yield of 5-enolpyruvylshikimate-3-phosphate (EPSP) from shikimate-3-phosphate (S3P) and phosphoenolpyruvate (PEP).

As shown in FIG. 2, EPSPS is comprised of two domains, one includes the three symmetric folding units shown as Units 1, 2 and 6, and the other includes the three symmetric folding units shown as Units 3, 4 and 5. Each unit is comprised of two parallel α-helices and four β-sheets. See Stallings, W. C. et al. *Proc Natl Acad Sci USA* 1991, 88, (11), 5046-50.

EPSP synthase is known to form an "open" conformation when there is no substrate, but turns to a "close" conformation when it forms a complex crystal structure with S3P or with glyphosate+S3P (Schonbrunn, E. et al. *Proc Natl Acad Sci USA* 2001, 98, (4), 1376-80). Mcdowell et al. (*J Biomol NMR* 2004, 28, (1), 11-29, 2004) modified the crystal structure of the complex of EPSP synthase, S3P and glyphosate by rotational-echo double-resonance NMR and obtained a three dimension structure which is consistent with the results from liquid NMR.

The substrate-binding sites and the catalytic sites of EPSP synthase are extensively investigated by methods such as chemical modification, gene mutation, and structural analysis (Schonbrunn, E. et al., supra; Mcdowell et al., supra; Anderson, K. S. et al. *J Biol Chem* 1990, 265, (10), 5567-72; Huynh, Q. K. et al. *J Biol Chem* 1988, 263, (24); 11636-9; Huynh, Q. K. et al. *J Biol Chem* 1988, 263, (2), 735-9; Padgette, S. R. et al. *J Biol Chem* 1988, 263, (4), 1798-802; Padgette, S. R. et al. *Arch Biochem Biophys* 1988, 266, (1), 254-62; Eschenburg, S. et al. *J Biol Chem* 2003, 278, (49), 49215-22; Mizyed, S. et al. *Biochemistry* 2003, 42, (23), 6986-95; Shuttleworth, W. A. et al. *Biochemistry* 1994, 33, (23), 7062-8; Shuttleworth, W. A. et al. *Arch Biochem Biophys* 1996, 334, (1), 37-42 Shuttleworth, W. A. et al. *Biochemistry* 1999, 38, (1), 296-302; Stauffer, M. E. et al. *Biochemistry* 2001, 40, (13), 3951-7; Stauffer, M. E. et al. *FEBS Lett* 2001, 499, (1-2), 182-6; McDowell, L. M. et al. *Biochemistry* 2004, 43, (21), 6606-11).

Furthermore, it is indicated that Lys-22, Arg-124, Asp-313, Arg-344, Arg-386 and Lys411 involve in PEP binding, Arg-27 involves in S3P binding, while Arg-100, Asp-242 and Asp-384 play important roles in conversion of the substrate-bound enzyme from an open conformation to a close one (Schonbrunn et al., *Proteins* 2000, k 40, (2), 290-8*: Biochemistry* 2000, 39, (9), 2164-73*; Proc Natl Acad Sci USA* 2000, 97, (12), 6345-9).

Selection of Divisional Sites

The inventors selected divisional sites in the regions which are not thought to affect the enzyme activity based on the structure of EPSPS.

When a divisional site locates between folding units, breakdown of covalent bond and insertion of methionine will generally not influence the formation of natural structure of the protein. The divided protein fragments form a functional protein structure by non-covalent interaction within the protein and by various non-covalent interactions such as hydrogen bond, salt bridge and hydrophobic interactions between two peptides, in order to be able to reconstitute the protein function. When a divisional site locates between folding units, formation of secondary structure of the complementary fragments will generally not be influenced, thus the fragment complementation occurs more easily. In the embodiments, seven divisional sites are selected in the joining regions between folding units for *E. coli* EPSPS. Six pairs of the divided protein fragments are capable of complementing EPSPS activity with relatively high complementary activity. As for *P. putida* EPSPS, three divisional sites are selected in the joining regions between folding units and all the three pairs of fragments are able to complement EPSPS activity.

When a divisional site locates in a joining region between α-helices and/or β-sheets, breakdown of covalent bond will generally not influence the formation of the α-helix or β-sheet, and insertion of methionine will generally have no significant effect on the formation of natural structure, thus fragment complementation occurs easily. In the embodiments for *E. coli* EPSPS, six divisional sites are selected in the joining regions between α-helices and/or β-sheets, wherein 5 pairs of the fragments complement EPSPS activity; another divisional site is selected in the joining region between β-sheets, and the resulting fragments also complement EPSPS activity. As for *P. putida* EPSPS, one divisional site is selected in a β-sheet and the resulting fragments complement EPSPS activity.

When a divisional site is selected in an α-helix or a β-sheet, fragment complementation of divided fragments are achievable for reconstituting the activity as long as the α-helix or β-sheet is tolerant to the breakdown of covalent bond or to the insertion of methionine or is not important for the activity. In the embodiments for *E. coli* EPSPS, seven divisional sites are selected in an α-helix or a β-sheet, wherein 3 pairs of the fragments complement EPSPS activity. As for *P. putida* EPSPS, one divisional site is selected in a β-sheet and the relevant fragments complement EPSPS activity.

When EPSPS is divided between two domains, the N-terminal peptide N240 and the C-terminal peptide C241 of *E. coli* EPSPS are co-purified as a complex. However, the enzyme activity of this complex is very poor, which may be resulted from that there is only one pair of hydrophobic interaction regions in N240/C241 complex and the protein structure is thus unstable. As for *P. putida* EPSPS, three divisional sites are tested between two domains, while all the fragments are substantively not capable of complementing EPSPS activity. Accordingly, the EPSPS fragments obtained by dividing in the joining regions between domains could not reconstitute EPSPS activity.

In summary, the inventors successfully divide *E. coli* EPSPS at 14 sites, 6 of them located in the joining regions between folding units, 3 of them located in the joining regions between an α-helix and a β-sheet, 2 of them located in the joining regions between β-sheets, 2 of them located in β-sheets and 1 of them located in an α-helix. By using these sites, the gene of *E. coli* EPSPS is divided into different N-terminal fragments and their relevant C-terminal fragments. Each N-terminal fragment and its relevant C-terminal fragment are carried separately on two compatible plasmids and are expressed. The resulting N-terminal protein fragment or its relevant C-terminal protein fragment alone does not exhibit EPSPS activity, while the association in vivo of the two fragments complement EPSPS activity.

Similarly, in another embodiment, the *P. putida* glyphosate-tolerant EPSPS is divided at 5 sites, wherein 3 sites locates in the joining regions between folding units, 1 in a joining region between an α-helix and a β-sheet, and 1 in a β-sheet. The resulting fragments also complement EPSPS activity.

The fact that EPSPS activity can be reconstituted by fragment complementation suggests the specific nature of the internal non-covalent interaction of this protein, which makes the fragments form a natural active structure exclusively and no other structure can be formed. In addition, the achievement of fragment complementation of the protein indicates that the protein keeps the structure stable even if covalent bonds are broken in some regions. That is to say, covalent bonds are not essential, non-covalent interactions such as hydrogen bond, salt bridge, and hydrophobic interaction are enough for the tight joint of two peptides. Hydrophobic interaction may be more important for EPSPS fragment complementation. The EPSPS fragment pairs have two potential hydrophobic-interaction regions which form two "hooks" to keep the protein stable.

A number of complexes are formed from fragment pairs in the present invention, but the amount of the purified proteins varies greatly. This indicates that the fragment complementation is always achievable in vivo but the form of the complexes from fragment pairs may be more or less difficult in different cases. The breakdown of a covalent bond has a significant effect on protein structural stability in some regions, while in some other regions, this effect is less. Introduction of one methionine (the amino acid encoded by start codon) into a C-terminal peptide may have effects on stability of the protein structure, so that protein fragment complementation can not occur.

Complex N240/C241 of *E. coli* EPSPS is also co-purified in large amounts, but fails to complement the growth of aroA gene-mutant *E. coli* strain AB2829 on a restrictive medium, because the EPSPS activity of the Complex N240/C241 is much lower than that of the wild type full length EPSPS. The loss of activity possibly dues to two reasons: firstly, the divisional site of N240/C241 is very close to Asp242 which plays a very important role in the structural conversion upon substrate binding, and the introduction of one methionine into C241 may destroy the action of Asp242 which leads to the lose of enzyme activity; secondly, N240/C241 divides at a site between the two domains and the resulting complex has only one pair of hydrophobic interaction regions. Although the hydrophobic interaction between the regions is sufficient to make the two protein fragments form a complex, the structure of the complex may differ from that of the wild type protein in the absence of another pair of hydrophobic interaction region, thus the enzyme activity is lost. Accordingly, a divisional site should be selected based on the effect of the structural changes on enzyme activity.

Localization of EPSP Synthase in Plant Cell

It was found that the aromatic amino acid biosynthesis takes place in chloroplast of plants (Bickel et al. Phytochemistry 17: 119-124, 1978). It was then demonstrated that the EPSP synthase locates in the endo-membrane of chloroplast in plants (Mousdale et al. Planta, 1987, 170:1~6; Plant Physiol., 1987, 83:229~231; J Biol Chem 1988 Oct. 15; 263. (29):15104-9; Mol Gen Genet. 1994 Dec. 1; 245(5):616-22; Mol Gen Genet. 1993 June; 239(3):416-24). In Petunia, the molecular weight of precursor EPSP synthase (precursor EPSPS) is 55 kDa with the first 72 amino acid residues as a leading peptide, and the molecular weight of mature EPSPS is 48 kDa, which is formed by processing, cutting and transferring the precursor EPSPS after its entry into chloroplast (Della-Cioppa et al., Bio/Technology 1987(5): 579~584). A leading peptide plays an important role in entry of a precursor peptide into chloroplast. When a microbial EPSP synthase gene is introduced into plant cells, a nucleotide sequence encoding a plant leading peptide is added prior to the gene, otherwise the expressed microbial EPSPS, which has no natural leading peptide, can not enter into chloroplast.

Use

EPSPS fragment complementation technique of the present invention can be used in transgenic plants, in order to prevent the ecological risk caused by glyphosate-tolerant gene spreading. For instance, the N-terminal fragment of EPSPS is expressed in the nuclear chromosome of a plant, while the C-terminal fragment is expressed in the chloroplast. Expression of either of the EPSPS fragments alone does not bring about EPSPS activity, thus the gene spread into other plants lacks advantages for selection. The two EPSPS fragments complement in chloroplast to reconstitute EPSPS activity upon co-expression, which makes the plant become glyphosate tolerant. Alternatively, genes encoding two relevant EPSPS fragments may be inserted into different positions within the same chloroplast genome. In this case, the chance for both the two genes to be transferred into the chromosomes is significantly reduced and the chance for gene spreading is greatly decreased. For the method to control the cell process in plants, please see WO2004/046359 and WO2004/046360.

DESCRIPTION OF THE DRAWINGS

FIG. 2 shows the structure of EPSPS and selection of divisional sites.

FIG. 7$b$ shows Western blot of native-PAGE of $E.$ $coli$ EPSPS. 1: N218+C219 (get together after individual renaturation); 2: blank control; 3: co-renatured N218/C219; 4: blank control; 5: wild type EPSPS.

EXAMPLES

Example 1

Reconstitution of $E.$ $coli$ EPSPS

Figure 1:
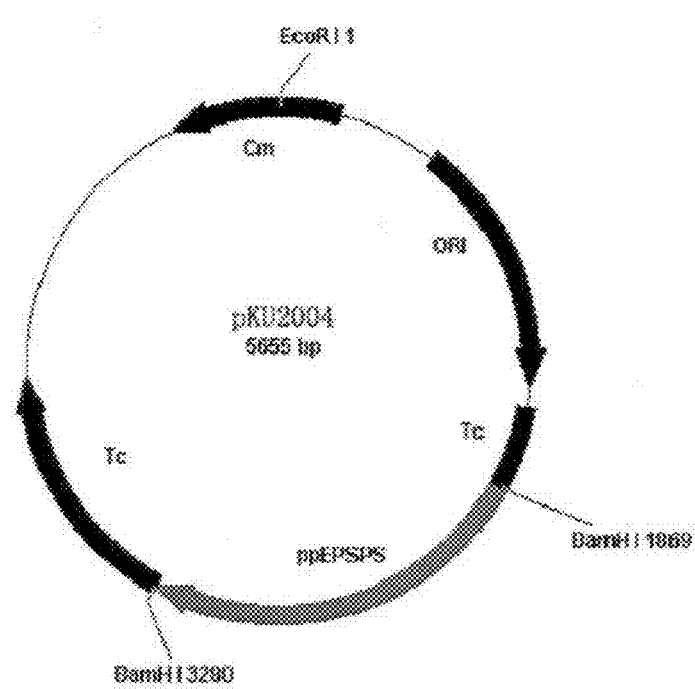
FIG. 1 shows plasmid pKU2004.
Figure 2A:
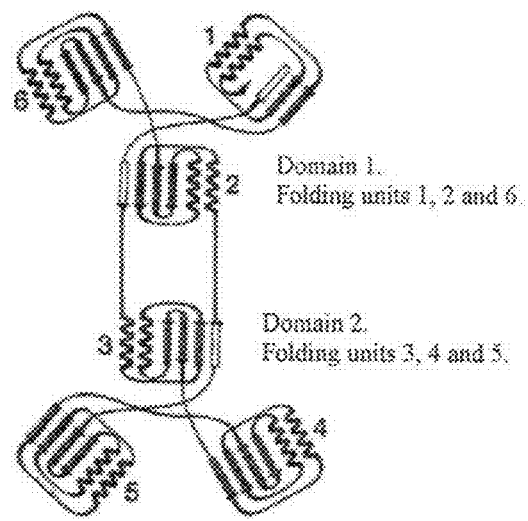
FIG. 2A shows the topological structure of EPSPS.
Figure 2B:
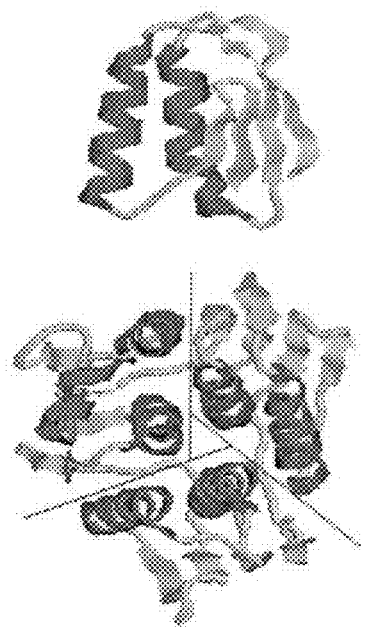
FIG. 2B shows a structure unit of EPSPS.

1 Materials and Methods
1.1 Strains and Plasmids

The strains and plasmids used in this study are listed in Table 1.

TABLE 1

Bacterial strains and plasmids used in this study

| strain/plasmid | features | origin/reference |
|---|---|---|
| $E.$ $coli$ strain | | |
| DH5α | supE44ΔlacU169hsdR17recA1gyrA96thi-1relA1 | Hanahan D., J Mol Biol 1983; 166: 557-80 |
| AB2829 | aroA354 | Yale University |
| B121(DE3) | | stragene |
| BA⁻ | BL21(DE3)⁻aroA, Ap$^R$ | This study |
| Plasmid | | |
| pUC18 | ColE1, lacZ', Ap$^R$ | Norrander et al., 1983 |
| pBluescript-SK | ColE1, lacZ', Ap$^R$ | Stratagene |
| pET-28a | ColE, expression plasmid, Km$^R$ | Novagen |
| pACYC184 | Cm$^R$ | Chang, A. C. et al. 1978. J Bacteriol 134: 1141-56 |
| pBR322 | ColE1, Ap$^R$ | Schaeffer, F. et al., 1982 EMBO J. 1, 99-105 |
| pKO3 | Cm$^R$ | Link, A. J. et al. 1997. J. Bacteriology 179: 6228-6237 |
| pKU2005 | pUC18 derived plasmid with aroA$_{E.\ coli}$, Ap$^R$ | This study |
| pKU2006 | pACYC184 derived plasmid with aroA$_{E.\ coli}$, Cm$^R$ | This study |
| pKU2007 | pACYC184 derived plasmid with aroA$_{E.\ coli}$-G96A, Cm$^R$ | This study |
| pKU2008 | pET-28a derived plasmid with $E.$ $coli$ aroA, Km$^R$ | This study |
| pKU2009 | pET-28a derived plasmid with $E.$ $coli$ aroA, Km$^R$ | This study |
| pKU2010 | pET-28a derived plasmid with $E.$ $coli$ aroA-G96A, Km$^R$ | This study |
| pKU2011 | pET-28a derived plasmid with $E.$ $coli$ aroA-G96A, Km$^R$ | This study |

TABLE 1-continued

Bacterial strains and plasmids used in this study

| strain/plasmid | features | origin/reference |
|---|---|---|
| pKU2100 | PBR322 derived plasmid with aroA$_{E.\ coli}$, Ap$^R$ | This study |
| pKU2101 | pACYC184 derived plasmid with N218-aroA$_{E.\ coli}$, Cm$^R$ | This study |
| pKU2102 | pBR322 derived plasmid with C219-aroA$_{E.\ coli}$, Ap$^R$ | This study |
| pKU2107 | pBR322 derived plasmid with aroA$_{E.\ coli}$-G96A, Ap$^R$ | This study |
| pKU2110 | pACYC184 derived plasmid with N245-aroA$_{E.\ coli}$, Cm$^R$ | This study |
| pKU2125 | pBR322 derived plasmid with C228-aroA$_{E.\ coli}$, Ap$^R$ | This study |
| pKU2126 | pBR322 derived plasmid with C235-croA$_{E.\ coli}$, Ap$^R$ | This study |
| pKU2127 | pET-28a derived plasmid with N218-E. coli aroA, Km$^R$ | This study |
| pKU2130 | pBR322 derived plasmid with C246-aroA$_{E.\ coli}$, Ap$^R$ | This study |
| pKU2137 | pACYC184 derived plasmid with N234-aroA$_{E.\ coli}$, Cm$^R$ | This study |
| pKU2138 | pACYC184 derived plasmid with N227-aroA$_{E.\ coli}$, Cm$^R$ | This study |
| pKU2154 | pBluscript-SK derived plasmid with aroA$_{E.\ coli}$, Ap$^R$ | This study |
| pKU2159 | pET-28a derived plasmid with E. coli aroA, Km$^R$ | This study |
| pKU2195 | pBluscript-SK derived plasmid with C219-aroA$_{E.\ coli}$, Ap$^R$ | This study |
| pKU2203 | pET-28a derived plasmid with N218-E. coli aroA, Km$^R$ | This study |
| pKU2205 | pET-28a derived plasmid with C218-E. coli aroA, Km$^R$ | This study |
| pKU2223 | pBluscript-SK derived plasmid with a part of the upstream sequence of aroA$_{E.\ coli}$ | This study |
| pKU2224 | pBluscript-SK derived plasmid with bla gene | This study |
| pKU2225 | pBluscript-SK derived plasmid with the downstream sequence of aroA$_{E.\ coli}$ | This study |
| pKU2227 | pBluscript-SK derived plasmid with the upstream and downstream sequences of aroA$_{E.\ coli}$ | This study |
| pKU2228 | pBluscript-SK derived plasmid with the upstream and downstream sequences of aroA$_{E.\ coli}$ and the bla gene | This study |
| pKU2229 | pKO3 derived plasmid with the upstream and downstream sequences of aroA$_{E.\ coli}$ and the bla gene | This study |
| pKU2249 | pET-28a derived plasmid with N245-E. coli aroA, Km$^R$ | This study |
| pKU2250 | pET-28a derived plasmid with C246-E. coli aroA, Km$^R$ | This study |
| pKU2262 | pACYC184 derived plasmid with N240-aroA$_{E.\ coli}$, Cm$^R$ | This study |
| pKU2263 | pBR322 derived plasmid with C241-aroA$_{E.\ coli}$, Ap$^R$ | This study |
| pKU2266 | pET-28a derived plasmid with N240-E. coli aroA, Km$^R$ | This study |
| pKU2267 | pACYC184 derived plasmid with T7 promoter and N218-aroA$_{E.\ coli}$, Cm$^R$ | This study |
| pKU2268 | pACYC184 derived plasmid with T7 promoter and N240-aroA$_{E.\ coli}$, Cm$^R$ | This study |
| pKU2269 | pET-28a derived plasmid with N227-E. coli aroA, Km$^R$ | This study |
| pKU2274 | pACYC184 derived plasmid with T7 promoter and N227-aroA$_{E.\ coli}$, Cm$^R$ | This study |
| pKU2275 | pACYC184 derived plasmid with T7 promoter and N234-aroA$_{E.\ coli}$, Cm$^R$ | This study |
| pKU2276 | pET-28a derived plasmid with C228-E. coli aroA, Km$^R$ | This study |
| pKU2277 | pET-28a derived plasmid with C235-E. coli aroA, Km$^R$ | This study |
| pKU2278 | pET-28a derived plasmid with C241-E. coli aroA, Km$^R$ | This study |
| pKU2282 | pET-28a derived plasmid with C246-E. coli aroA, Km$^R$ | This study |
| pKU2283 | pET-28a derived plasmid with C219-E. coli aroA, Km$^R$ | This study |
| pKU2287 | pACYC184 derived plasmid with T7 promoter and N240-aroA$_{E.\ coli}$, Cm$^R$ | This study |
| pKU2289 | pACYC184 derived plasmid with T7 promoter and N245-aroA$_{E.\ coli}$, Cm$^R$ | This study |

Ap, ampicillin;
Cm, chloromycetin;
Km, kanamycin;
$^R$, resistance;
Δ, deletion;
::, fusion.

1.2 Medium

| LB media: | amount per liter: |
|---|---|
| tryptone | 10 g |
| yeast extract | 5 g |
| NaCl | 10 g |

Water was added up to 1 liter and pH was adjusted to around 7.0-7.5 with 2M NaOH. For solid media, 1.5% agar was added. The medium is autoclaved at 121° C., 15 pounds for 20 min before use.

Ap was added to a concentration of 50 μg/ml to select ampicillin resistant strains.

Km was added to a concentration of 25 μg/ml to select kanamycin resistant strains.

Cm was added to a concentration of 25 μg/ml to select chloromycetin resistant strains.

Restrictive M63 Medium:

13.6 g/L KH$_2$PO$_4$, 0.5 mg/L FeSO$_4$-7H$_2$O, 20 mM (NH$_4$)$_2$SO$_4$, 0.4% glucose, 1 mM magnesium sulfate, 0.5 mg/L vitamin B1.

1.3 Reagents

Restriction endonuclease, T$_4$DNA ligase, TaqDNA polymerase, DNA marker (Takara). Coomassie brilliant blue G250, enolpyruvate (sigma), shikimate-3-phosphate (a gift from Prof. Amrehin); HisTrap HP kit (Amersham Biosciences), goat anti-rabbit IgG (promega); all the other chemicals were reagents of analytical grade.

1.4 Genetic Manipulation

Preparation of plasmid DNA, digestion with restriction endonuclease, ligation reaction, horizontal agarose electrophoresis in Tris-boric acid-EDTA buffer, polyacrylamide gel electrophoresis and Western blot and the like were carried out according to standard procedures (Molecular Cloning: A Laboratory Manual, 2nd edition. (Sambrook, Fritsch and Maniatis, eds.), Cold Spring Harbor Laboratory Press, 1989).

1.5 Plasmid Construction a. Construction of pKU2008, pKU2009

An *E. coli* aroA gene was amplified using primer 11: 5'-CGGGATCCAGGTCCGAAAAAAAACGCCGAC 3' and primer 12: 5'-CGGGATCCATGGAATCCCTGACGTTACA 3' and taking pKU2004 as a template, and was ligated into pET28a vector to obtain pKU2008. The EPSPS encoded by this plasmid was a fusion protein with His-tag at the N-terminus. pKU2008 was cleaved with NcoI and self-ligated to obtain pKU2009, which encodes an *E. coli* wild type EPSPS.

b. Construction of pKU2100 Series Plasmids (Encoding C-Terminal Peptides of EPSPS)

PCR amplification was run using primer 13: 5'-TGAGTGACTGACTTTAAGAAGGAGA TATAC3' and primer 14: 5-CGGGATCCTCACTGATTTTCAATTTCAACAC 3' and taking pKU2009 as a template. The resulting product was digested with BamHI and was ligated into the EcoRV and BamHI sites of pBR322 to obtain plasmid pKU2100. Genes encoding C-terminal fragments of *E. coli* EPSPS were amplified taking pKU2009 as a template and using corresponding primers. The resulting products were ligated into the NcoI and BamHI sites of pKU2100 to obtain plasmids pKU2102, pKU2125, pKU2126, pKU2130 and pKU2263, respectively. These plasmids encodes C-terminal peptides of *E. coli* EPSPS (Table 1, FIG. 3).

c. Construction of pACYC184 Series Plasmids (Encoding N-Terminal Peptides of EPSPS)

Genes encoding N-terminal fragments of *E. coli* EPSPS are amplified by PCR taking pKU2009 as a template and using corresponding primers. The resulting products were ligated into EcoRV and BamHI sites of pACYC184 to obtain plasmids pKU2101, pKU2125 pKU2110, pKU2137, pKU2138 and pKU2262, respectively. These plasmids encodes amino acid sequences at the N-terminus of *E. coli* EPSPS (Table 1, FIG. 3).

d. Construction of pET28a Series Expression Plasmids

The pBR322 series plasmid constructed in Step b and the pACYC184 series plasmid constructed in Step c were digested with NcoI and BamHI respectively. Suitable fragments were recovered and ligated into pET28a vectors to obtain pET28a series expression plasmids expressing N-terminal or C-terminal peptides of EPSPS (Table 1).

e. Construction of pACYC-T7 Series Expression Plasmids

The pET28a plasmids expressing N-terminal peptides of EPSPS were digested with BglII and SalI respectively. The desired fragments were recovered and ligated into BamHI and SalI sites of pACYC184 vectors to obtain the pACYC-T7 series expression plasmids (Table 1, FIG. 3).

f. Construction of pET28a Series Expression Plasmids (Expressing Fusion Proteins of C-Terminal Peptides with His-taq)

Figure 3:
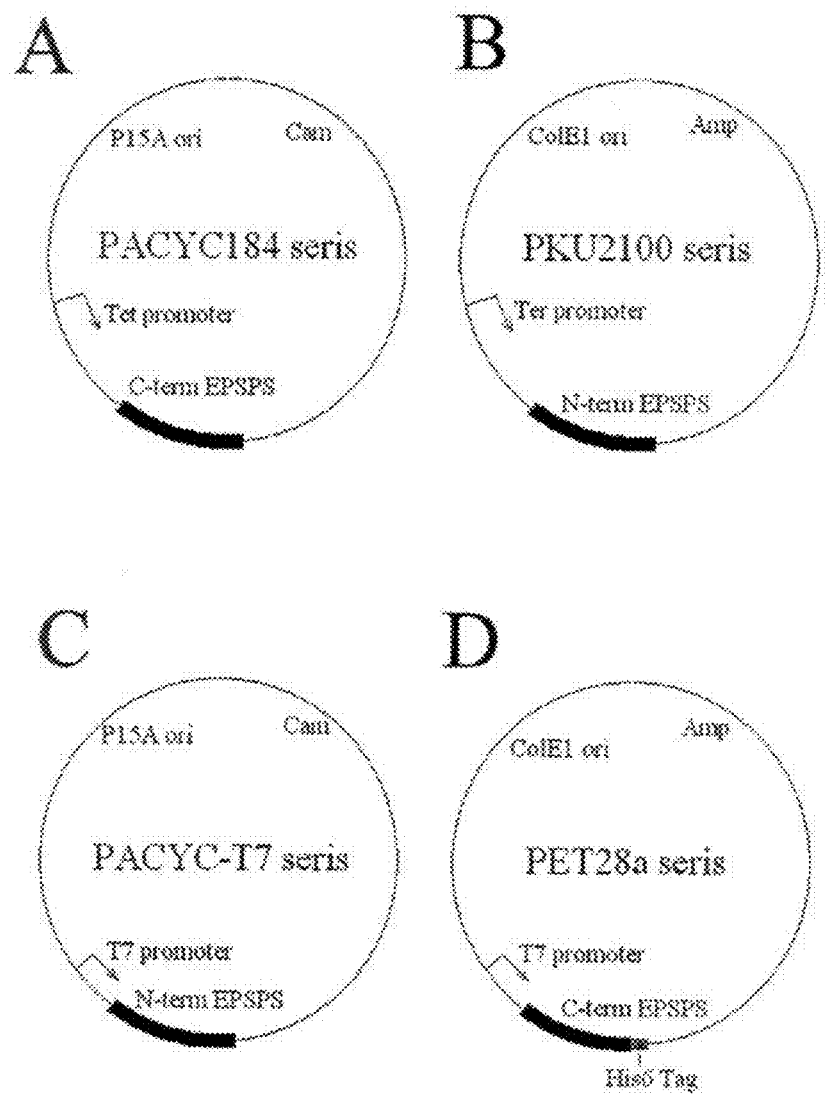
FIG. 3 shows the plasmid construction. A) A C-terminal fragment of EPSPS is subcloned next to a Tet promoter in pKU2100 vector. B) A N-terminal fragment of EPSPS is subcloned next to a Tet promoter in pACYC184 vector. C) A N-terminal part of the EPSPS encoding gene is subcloned next to a T7 promoter in a plasmid vector derived from pACYC184. D) A C-terminal part of EPSPS is constructed into pET28a vector, with a 6-His tag at the C-terminus.

Genes encoding different portions of *E. coli* EPSPS were amplified taking pKU2009 as a template and using corresponding primers. The resulting products were digested with XhoI and NcoI, and ligated into pET28a vectors to obtain pET28a series expression plasmids. The EPSPS encoded by the series plasmids was fused with 6 histidines at the C-terminus in order to be purified by a nickel column (FIG. 3).

g. Construction of Plasmid pKU2229 for Strain Mutation

A ~600 bp fragment upstream of aroA gene in the chromosome of *E. coli* BL21 (DE3) was PCR amplified taking the chromosome as a template. The fragment was ligated into the BamHI and HindIII sites of pBlueScript (stratagene) to obtain plasmid pKU2223. A bla gene of ~900 bp was PCR amplified taking plasmid pBlueScript as a template and was ligated into the HindIII and EcoRI sites of pBlueScript (stratagene) to obtain plasmid pKU2224.

A ~500 bp fragment downstream of aroA gene in the chromosome of *E. coli* BL21 (DE3) was PCR amplified taking the chromosome as a template. The fragments were ligated into the EcoRI and SalI sites of pBlueScript (stratagene) to obtain plasmid pKU2225. pKU2225 was digested by enzyme and the resulting fragments were ligated into the EcoRI and SalI sites of pKU2223 to obtain plasmid pKU2227. pKU2224 was digested by enzyme and the resulting fragments were ligated into the HindIII and EcoRI sites of pKU2227 to obtain plasmid pKU2228. A fragment between the BamHI site and SalI site of pKU2228 was recovered by enzyme digestion and ligated into pKO3 to obtain plasmid pKU2229.

All the plasmids are confirmed of correct sequence by sequencing.

1.6 Construction of Mutant Strain BA$^-$

The aroA gene of BL21 (DE3) was replaced with a bla gene, a gene conferring resistance to ampicillin, by using plasmid pKU2229 derived from pKO3. Specifically, pKU2229 was introduced into BL21 (DE3). A colony was picked up and diluted to spread on solid LB plate comprising antibiotics Ap and Cm, and was incubated overnight at 43° C. Since a pKO3 replicon was not able to originate replication normally at 43° C., a strain could grow on the plate containing antibiotics Ap and Cm at 43° C. only if pKU2229 was recombined into the chromosome of the strain. One recombinant colony was picked up and diluted to spread onto the LB medium containing only Ap antibiotics and 5% sucrose, and was cultured overnight. Bacteria carrying a Sac B gene are not able to grow on the medium containing 5% sucrose because the protein encoded by the Sac B gene in pKO3 is toxic to bacterial cells due to degradation of sucrose. Accordingly, colonies grown on LB medium containing Ap antibiotics and 5% sucrose are the ones in which both aroA gene and sacB gene are deleted by a further homologous recombination. Several colonies were streaked on Cm plate and M63 plate to confirm the deletion of aroA gene. Total DNA was extracted from these colonies and PCR amplification was performed to confirm the replacement of aroA gene with bla gene.

1.7 In Vivo Complementation

The pKU2100 plasmid constructed as described above and corresponding pACYC1184 plasmid were introduced separately or together into the strain AB2829 deficient in *E. coli* aroA gene. Then, the strain was streaked on solid M63 restrictive medium and cultured overnight to determine the growth.

1.8 Determination of Growth Curve aroA gene-mutant *E. coli* strains AB 2829 carrying plasmid pKU2004, pKU2006 or pKU2007 were inoculated in liquid LB medium and incubated overnight. A sample of the culture was centrifuged at 4000 rpm for 3 min and re-suspended in 0.9% physiological saline. After a further centrifugation, the supernatant was discarded. The pellets were re-suspended in physiological saline and inoculated at an initial concentration of OD$_{600}$ 0.04 into a liquid media comprising 0, 50 or 100 mM glyphosate for overnight culture at 37° C. Absorption (OD$_{600}$) was measured at intervals.

1.9 Protein Expression and Purification

BA$^-$ strain comprising the plasmid of interest was inoculated into liquid LB medium supplemented with corresponding antibiotics and incubated on a shaker at 37° C. till OD$_{600}$ 0.75. IPTG was added to a final concentration of 0.5 mM into the medium and incubation was performed overnight at 15° C. A sample of the culture was centrifuged at 5000 rpm, 4° C. to collect cell pellets, which were then resuspended 10:1 by volume in Buffer A (50 mM Tris-HCl (pH 7.8), 0.4 mM DTT). The cells were broken by ultrasonication and centrifuged at 8000 rpm, 4° C. for 60 min.

The supernatant was subjected to protein purification by using a HisTrap HP kit (Amersham Biosciences) according to the manufacturer's protocol. The purified proteins were concentrated in Buffer A using a Millipore Biomax membrane (10 kDa) and stored at 4° C.

1.10 Preparation of Multiclonal Antibody Against EPSPS

Proteins encoded by pKU2008 in BL21 (DE3) strain were expressed and purified as described above, and then concentrated and resuspended in PBS buffer for use as an antigen to immunize rabbit. After four immunizations and one boost, serum was collected (this process was accomplished by Institute of Genetics, Chinese Academy of Science). The titre of the antibody was determined by ELASA prior to further use.

1.11 Polyacrylamide Gel Electrophoresis

SDS-PAGE (polyacrylamide gel electrophoresis) was run with the upper stacking gel of 5% and the lower separation gel of 16%. Native-PAGE was run with a gel of 10%. See, e.g. Sambrook et al., supra for the preparation of gel and buffer and the method of electrophoresis.

1.12 Determination of Circular Dichroism Spectra (CD Spectra)

The far ultraviolet- and near ultraviolet-CD spectra were determined on a Jobin Yvon CD6 connected with a thermostatic water-bath circulation controller. Each curve was obtained using average values from four measures. The measurement was performed at 8° C. A 1-cm pathlength cylinder quartz cuvette was used for the near ultraviolet CD spectra, and a 0.1-mm pathlength cylinder quartz cuvette was used for the far ultraviolet CD spectra.

1.13 Immunoblot of EPSPS Fragment

Membrane transfer and immunoblot were carried out according to Sambrook et al., supra. Briefly, the protein was transferred onto a cellulose nitrate membrane after subjected to 16% SDS-PAGE. The membrane was incubated with 1:2000 diluted rabbit multiclonal antibody. The resulting antigen-antibody complex was further reacted with a secondary antibody goat anti-rabbit IgG conjugated with horseradish peroxidase (promega) to form a complex. The color was developed upon the degradation of DAB (Sino-American Biotechnology Company) by horseradish peroxidase according to the manufacture's protocol.

1.14 Determination of EPSPS Activity

Determination of Enzyme Activity (1) 95 μl substrate (50 mmol/L HEPES buffer (pH 7.5), 1 mmol/L PEP, 1 mmol/L S3P) was pre-warmed at 28☐ in an incubator for 5 min.

(2) 5 μl enzyme was added and the reaction was kept in an incubator at 28☐ for 1-20 min (depends on the enzyme activity). After that, 800 μl MG/AM/NP was added and the reaction was mixed for 1 min.

(3) 100 μl 34% sodium citrate was added and the reaction was mixed for half an hour. The OD$_{660}$ was measured on a spectrometer.

1.15 In Vitro Complementation

The N-terminal and C-terminal peptides of EPSPS were expressed separately in BA$^-$. The cells were collected by centrifugation and then broken by ultrasonication. Electrophoresis was run to see whether the proteins of interest precipitated mainly as inclusion bodies. The precipitate was washed first with Buffer B (50 mM Tris-HCl (pH 7.8), 1 mM EDTA, 0.05% Triton-100) for three times, then with 1M NaCl for three times, then with Buffer C (50 mM Tris-HCl (pH 7.8), 1 mM EDTA, 1M urea) for three times, and finally with distilled water for three times. The precipitate was then added into Buffer A containing 8M urea. After centrifugation, the supernatant was dialyzed against Buffer D (50 mM Tris-HCl (pH 7.8), 1 mM GSH, 0.5 mM GSSG) with 2M urea overnight and then against Buffer D for 36 hours. Concentration was carried out using PEG12000. The renatured product was analyzed by electrophoresis, immune reaction and enzyme activity assay.

2. Result of Fragment Complementation of *E. coli* EPSPS 2.1 In Vivo Complementation In order to test if EPSPS achieves fragment complementation after in vivo expression, genes encoding EPSPS N-terminal peptides were constructed into pACYC184, and genes encoding EPSPS C-terminal peptides were constructed into pBR322 (see the section Materials and Methods for the detailed construction method). Afterwards, these plasmids were introduced into aroA gene-mutant *E. coli* strain AB2829. EPSPS activity of the protein fragments encoded by these genes was determined by the growth of the strains on M63 restrictive medium. It was found that AB2829 strains carrying only N-terminal or C-terminal encoding genes are not able to grow on the M63 medium.

The pACYC184 and pBR322 plasmids are able to be expressed in the same bacterial cell since they have replicons p15A and ColE1 respectively. In this regard, a pACYC184 plasmid was co-introduced into aroA gene-mutant *E. coli* strain AB2829 together with a corresponding pKU2100 plasmid, wherein the N-terminal peptide encoded by the pACYC184 plasmid and C-terminal peptide encoded by the pKU2100 plasmid are the two fragments divided at the same site from EPSPS. The resulting strains are streaked on M63 restrictive medium, and cultured at 37° C. 16 hours later, AB2829 strains carrying N218/C219-encoding plasmids (pKU2101/pKU2102) or N227/C228-encoding plasmids (pKU2125/pKU2138) grow on the restrictive medium, while AB2829 strains carrying other three pairs of plasmids pKU2126/pKU2137(N234/C235), pKU2162/pKU2163 (N240/C241) or pKU2110/pKU2130 (N245/C246) fail to grow on the M63 medium. This indicated that EPSPS fragment pairs N218/C219 and N227/C228 complement EPSPS activity upon their in vivo expression, while the other three pairs of fragments not.

2.2 Purification and Determination of Complex of EPSPS Fragments

In order to determine whether the recovery of EPSPS activity is due to in vivo recombination of genes encoding EPSPS fragments which leads to a full length EPSPS, the protein fragments were purified and tested in vitro for enzyme activity and sizes to confirm that the recovery of EPSPS activity is due to fragment complementation. For this, plasmids are constructed for expression of EPSPS fragments under the control of T7 promoter, wherein the N-terminal fragments are constructed on pACYC184 vectors and the C-terminal fragments fused with 6 histidines are constructed on pET28a vectors (see the context above for the method of plasmid construction). If pairs of two fragments are able to form a natural structure, the N-terminal peptide will associate with the corresponding C-terminal peptide to form a complex which could be purified by attachment onto a nickel column.

In order to eliminate the effect of EPSPS encoded by aroA gene in the bacterial chromosome, a strain BA⁻ was obtained in which the aroA gene in *E. coli* BL21 was replaced by a bla gene encoding β-lactamase. The pairs of plasmids were introduced into a BA⁻ strain for co-expression. The cells were streaked on a M63 plate containing IPTG and cultured overnight for in vivo complementation. The result was consistent with the above description: BA⁻ cells carrying genes for N218/C219 or N227/C228 fragments grow on the M63 restrictive medium; BA⁻ cells carrying genes of the other three fragment pairs fails to grow on the M63 restrictive medium.

Figure 4:
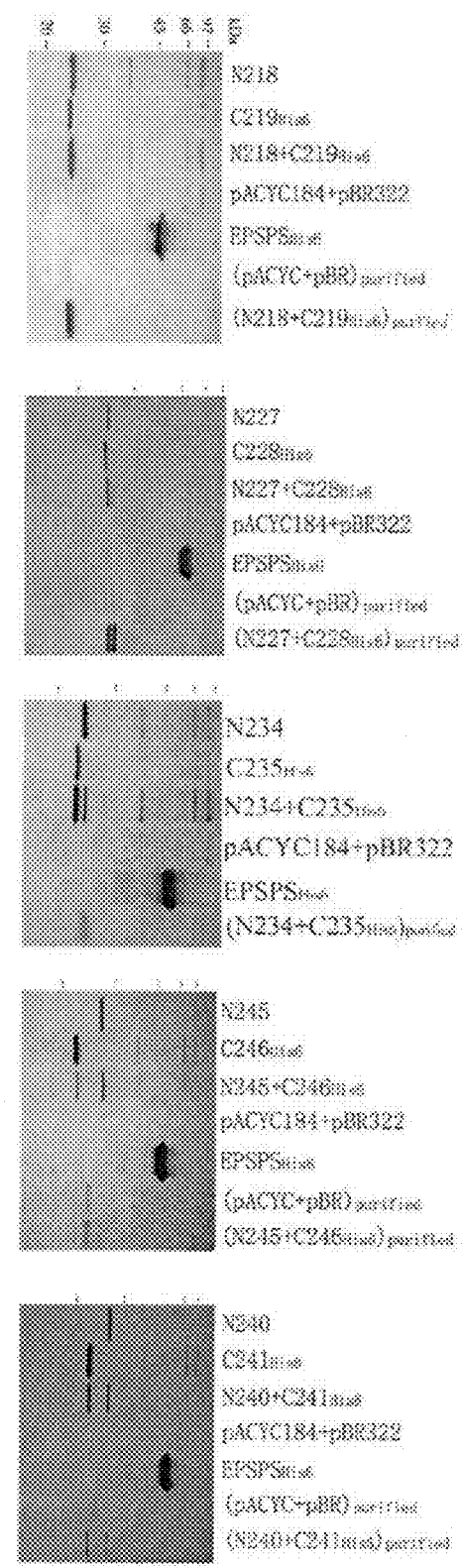
FIG. 4 shows the Western blot of EPSPS fragments. Cells expressing the indicated EPSPS are dissolved in SDS sample buffer. Equivalent amount of proteins (derived from ~0.8 μg wet cells) and the purified proteins are analyzed by SDS-PAGE and Western blot. Amounts of the following purified proteins are shown in the figure: N218/C219 (from ~150 ml wet cells), N227/C228 (from ~20 μg wet cells), N234/C235 (from ~500 μg wet cells), N240/C241 (from ~40 μg wet cells), N245/C246 (from ~500 μg wet cells) and pACYC184/pBR322 (from ~500 μg wet cells). The standard molecular weight is shown on the left side as in kilo-Dalton (kd).

The N-terminal peptides and the C-terminal peptides of EPSPS were expressed separately or together in BA⁻ cells and their expression are confirmed by SDS-PAGE. The co-expressed proteins were purified using a HisTrap HP kit, and probed by using an EPSPS antibody on SDS-PAGE (see the section Materials and methods for the detailed procedure). As shown in FIG. 4, the purified proteins comprise both the C-terminal and the corresponding N-terminal peptides and the sizes of these protein fragments are the same as expected. This indicated that the EPSPS fragments co-expressed in vivo are purified as complexes due to complementation. It was also obvious in the figures that the co-expressed fragments are not linked together to be a full length protein before or after purification, which indicates that no recombination and thus no full length EPSPS gene occurred in vivo. It was also shown by the activity assay that all of the purified proteins had EPSPS activity. In summary, EPSPS activity is recovered by fragment complementation of peptides expressed respectively in vivo.

The expression amount of N- and C-terminal peptides of EPSPS may vary. For example, the expression amount of N227 was much more than that of C228, but the ratio of N- and C-terminal fragments after purification was 1:1 in almost all cases. As shown in the figures, the amounts of N234/C235 and N245/C246 after purification were much less than that of the other three co-purified EPSPS. May be this is why they fail to complement EPSPS activity in vivo to make AB2829 grow on the restrictive medium. Although the amount of N240/C241 complex after purification was even more than that of N218/C219, it fails to support the growth of AB2829 on the restrictive medium because of the poor EPSPS activity.

2.3 Determination of Enzyme Activity

N218/C219 and N227/C228, which are purified with His-Trap HP kit, and a full length EPSPS were further purified on a Sephadex-G75 column. As a result, N218/C219, N227/C228 and the full length EPSPS shared the same elution peak, indicating that they were substantially the same in terms of molecular weight and structure. The enzyme activities and the Km values to substrates of these three proteins were measured. As shown in Table 2, the enzyme activities of EPSPS complexes N218/C219 and N227/C228 after fragment complementation were 70% and 64% of that of full length EPSPS, respectively, while the affinity to substrates changed little, which indicated that the structure of the reconstituted EPSPS was relatively stable.

TABLE 2

Enzymatic properties of EPSPS and the reconstituted EPSPS

| Enzyme (μM) | specific activity [b] (mol min⁻¹ mg⁻¹) | $K_m$ [PEP] [c] (μM) | $K_m$ [S3P] [d] |
|---|---|---|---|
| EPSPS | 44 ± 2 | 14 ± 3 | 45 ± 1 |
| 218/219 | 31 ± 3 | 18 ± 3 | 49 ± 3 |
| 227/228 | 28 ± 4 | 19 ± 3 | 49 ± 6 |

[a] Results from two individual experiments, each of which includes triplicates.
[b] For determination of the enzyme specific activity, the concentrations of PEP and S3P were both 1.0 mM.
[c] For determination of $K_m$[PEP], the concentration of S3P was kept as 1 mM while the concentration of PEP varied from 50 to 200 μM.
[d] For determination of $K_m$[S3P], the concentration of PEP was kept as 1 mM while the concentration of S3P varied from 50 to 200 μM.

2.4 Circular Dichroism Spectra (CD Spectra) Analysis

Figure 5:
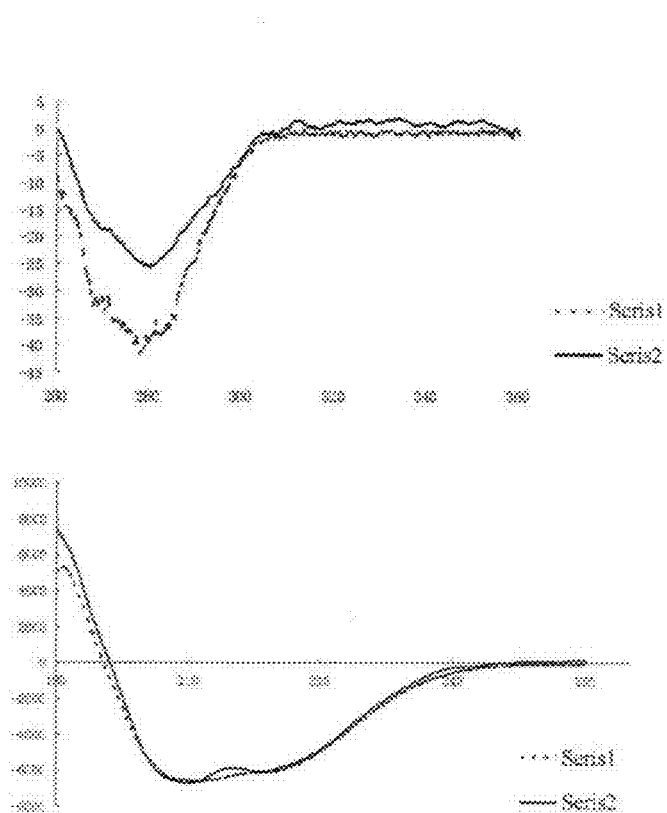
FIG. 5 shows the circular dichroism spectroscopy of EPSPS. Series 1 is for wild EPSPS and Series 2 is for N227/C228 complex.

In order to confirm whether the structure of the reconstituted EPSPS was the same as wild type EPSPS, circular dichroism spectroscopy was carried out for EPSPS and the complex N227/C228. There was no significant difference in far ultraviolet CD spectra between the EPSPS and N227/C228 (FIG. 5), which indicated that their secondary structures were almost the same. However, there was difference in near ultraviolet CD spectra (FIG. 5), which indicated that there was difference in structure between the reconstituted EPSPS and the wild type EPSPS.

2.5 In Vivo Complementation of Mutant EPSPS of *E. coli*

Figure 6:
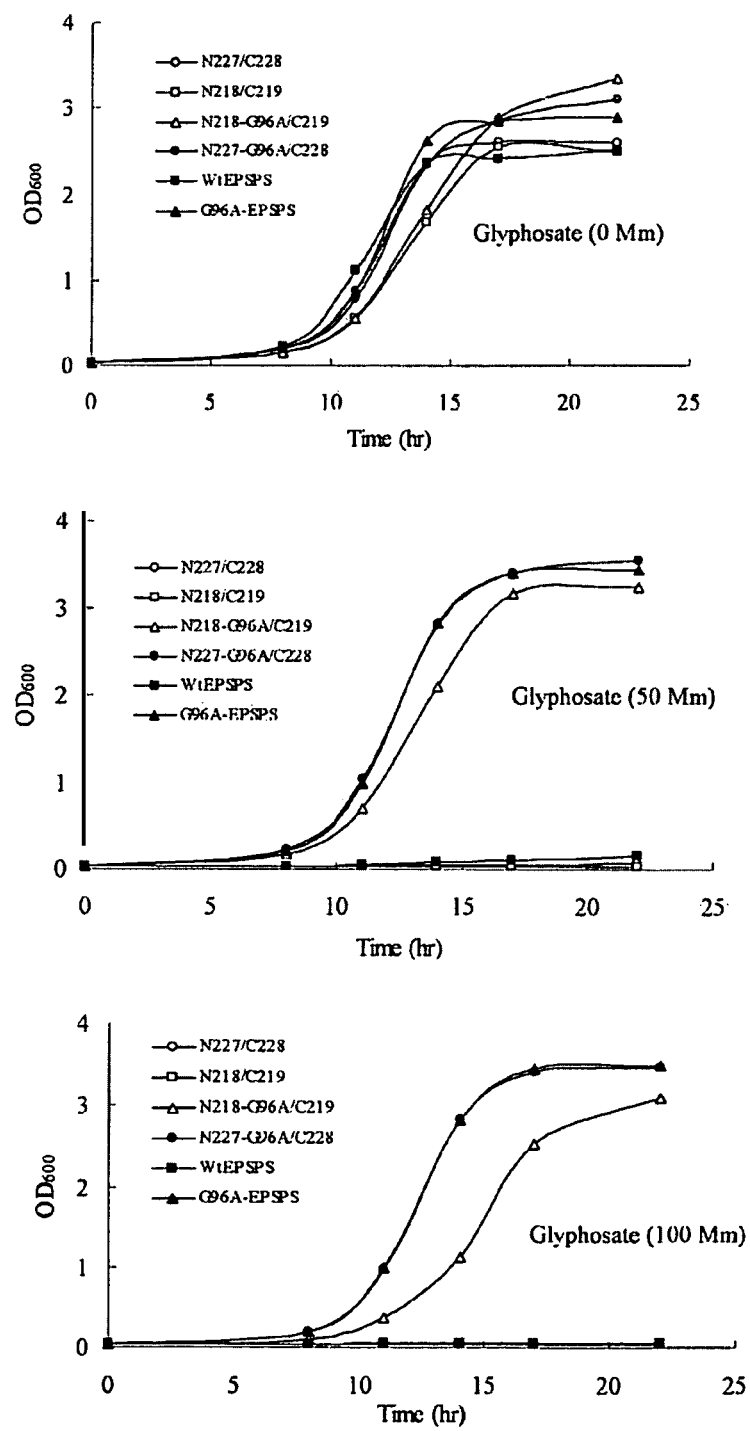
FIG. 6 shows the growth of aroA gene-deficient $E.$ $coli$ strain AB2829, which expresses different EPSPS, in the restrictive mediums (liquid M63 minimum medium in which glyphosate is added with the indicated concentrations).

In order to test whether the mutated EPSPS fragments perform functional complementation in vivo, plasmid pKU2105 and pKU2333 were constructed, which encode the N-terminal fragments N218-G96A and N227-G96A of *E. coli* EPSPS, respectively. They were introduced into aroA-mutant *E. coli* strain AB2829 (aroA–, from Yale University) together with their corresponding plasmids encoding C219 and C228 respectively. The growth was detected in the M63 restrictive media with different concentrations of glyphosate. As shown in FIG. 6, all the AB2829 strains grew well in M63 medium with no glyphosate without significant difference. In M63 medium containing 50 mM glyphosate, strains expressing the mutant full-length EPSPS (EPSPS-G96A) or the mutant complementary fragments (N227-G96A/C228 and N218-G96A/C219) grew well, while strains expressing wild type EPSPS or wild type complementary fragments were inhibited from growth. In the M63 medium containing 100 mM glyphosate, strains expressing EPSPS-G96A or N227-G96A/C228 still grew well while strains expressing N218-G96A/C219 did not grow as well as they did in the M63 medium containing 50 mM glyphosate, which might because that the N227-G96A/C228 complex is more easy to be formed in vivo.

2.6 In Vitro Reconstitution of EPSPS

Figure 7A:
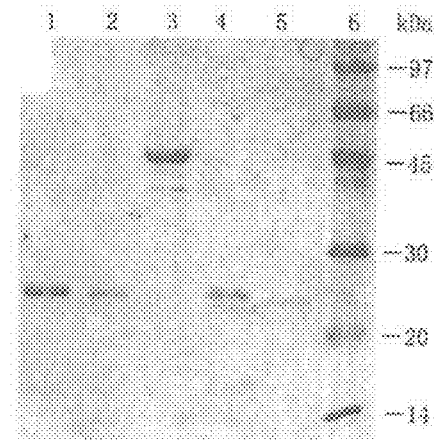
FIG. 7$a$ shows SDS-PAGE of $E.$ $coli$ EPSPS. 1: N218; 2: C219; 3: EcEPSPS; 4: co-renatured N218+c219; 5: N218+c219 (get together after individual renaturation); 6: standard molecular weight.
Figure 7B:
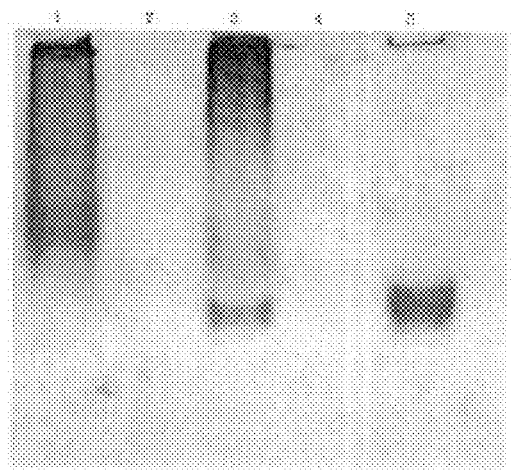

When protein fragments form an active complex by complementation in vivo, they are expected to form active complex in vitro. To verify this, EPSPS N-terminal peptide N218 and C-terminal peptide C219 were expressed separately. Inclusion bodies were formed in the presence of rich EPSPS fragments being expressed, and were subjected to purification and renaturation (see the section Materials and methods for the procedure). Result of electrophoresis after renaturation was shown in FIG. 7. As shown in FIG. 7a, each EPSPS fragment presented as expected and no full length EPSPS was found. In vitro co-renaturation of N218 and C219 leads to a band in native-PAGE which were consistent with that of wild type EPSPS, while the mixture of separately renatured N218 and C219 did not show this band. This indicates that a structure similar to that of wild type EPSPS could be formed upon in vitro co-renaturation of EPSPS. The activity assay also showed that complementation of EPSPS activity is achievable upon co-renaturation of N218/C219, but not upon mixture of separately renatured N218 and C219.

3. Correlations Between Fragment Complementation and Structure of EPSPS 3.1 the Strains and Plasmids Used are Show in the Table Below.

TABLE 3

Bacteria strains and plasmids used in this study

| strain/plasmid | features | Origin/Reference |
|---|---|---|
| *E. coli* strain | | |
| DH5α | supE44ΔlacU169hsdR17recA1gyrA96thi-1re1A1 | Hanahan D., J Mol Biol 1983; 166: 557-80 |
| AB2829 | aroA354 | Yale University |
| plasmid | | |
| pUC18 | ColE1, lacZ', $Ap^R$ | Norrander et al., 1983 |
| pBluscript-SK | ColE1, lacZ', $Ap^R$ | Stratagene |
| pET-28a | ColE1, expression plasmid, $Km^R$ | Novagen |
| pACYC184 | $Cm^R$ | Chang, A. C. et al. 1978. J Bacteriol 134: 1141-56 |
| pBR322 | ColE1, $Ap^R$ | Schaeffer, F. et al., 1982 EMBO J. 1, 99-105 |
| pKU2005 | pUC18 derived plasmid with aroA$_{E.\ coli}$, $Ap^R$ | This study |
| pKU2006 | pACYC184 derived plasmid with aroA$_{E.\ coli}$, $Cm^R$ | This study |
| pKU2007 | pACYC184 derived plasmid with aroA$_{E.\ coli}$ - G96A, $Cm^R$ | This study |
| pKU2008 | pET-28a derived plasmid with *E. coli* aroA, $Km^R$ | This study |
| pKU2009 | pET-28a derived plasmid with *E. coli* aroA, $Km^R$ | This study |
| pKU2010 | pET-28a derived plasmid with *E. coli* aroA-G96A, $Km^R$ | This study |
| pKU2011 | pET-28a derived plasmid with *E. coli* aroA-G96A, $Km^R$ | This study |
| pKU2100 | PBR322 derived plasmid with aroA$_{E.\ coli}$, $Ap^R$ | This study |
| pKU2101 | pACYC184 derived plasmid with N218-aroA$_{E.\ coli}$, $Cm^R$ | This study |
| pKU2102 | pBR322 derived plasmid with C219-aroA$_{E.\ coli}$, $Ap^R$ | This study |
| pKU2103 | pACYC184 derived plasmid with N238-aroA$_{E.\ coli}$, $Cm^R$ | This study |
| pKU2104 | pBR322 derived plasmid with C239-aroA$_{E.\ coli}$, $Ap^R$ | This study |
| pKU2110 | pACYC184 derived plasmid with N245-aroA$_{E.\ coli}$, $Cm^R$ | This study |
| pKU2111 | pACYC184 derived plasmid with N259-aroA$_{E.\ coli}$, $Cm^R$ | This study |
| pKU2124 | pBR322 derived plasmid with C225-aroA$_{E.\ coli}$, $Ap^R$ | This study |
| pKU2125 | pBR322 derived plasmid with C228-aroA$_{E.\ coli}$, $Ap^R$ | This study |
| pKU2126 | pBR322 derived plasmid with C235-aroA$_{E.\ coli}$, $Ap^R$ | This study |
| pKU2129 | pACYC184 derived plasmid with N31-aroA$_{E.\ coli}$, $Cm^R$ | This study |
| pKU2130 | pBR322 derived plasmid with C246-aroA$_{E.\ coli}$, $Ap^R$ | This study |
| pKU2131 | pBR322 derived plasmid with C260-aroA$_{E.\ coli}$, $Ap^R$ | This study |
| pKU2135 | pBR322 derived plasmid with C299-aroA$_{E.\ coli}$, $Ap^R$ | This study |
| pKU2136 | pACYC184 derived plasmid with N298-aroA$_{E.\ coli}$, $Cm^R$ | This study |
| pKU2137 | pACYC184 derived plasmid with N234-aroA$_{E.\ coli}$, $Cm^R$ | This study |
| pKU2138 | pACYC184 derived plasmid with N227-aroA$_{E.\ coli}$, $Cm^R$ | This study |
| pKU2139 | pACYC184 derived plasmid with N224-aroA$_{E.\ coli}$, $Cm^R$ | This study |
| pKU2148 | pACYC184 derived plasmid with N165-aroA$_{E.\ coli}$, $Cm^R$ | This study |
| pKU2149 | pBR322 derived plasmid with C166-aroA$_{E.\ coli}$, $Ap^R$ | This study |
| pKU2150 | pACYC184 derived plasmid with N371-aroA$_{E.\ coli}$, $Cm^R$ | This study |
| pKU2151 | pBR322 derived plasmid with C372-aroA$_{E.\ coli}$, $Ap^R$ | This study |
| pKU2290 | pACYC184 derived plasmid with N67-aroA$_{E.\ coli}$, $Cm^R$ | This study |
| pKU2291 | pACYC184 derived plasmid with N73-aroA$_{E.\ coli}$, $Cm^R$ | This study |
| pKU2292 | pACYC184 derived plasmid with N84-aroA$_{E.\ coli}$, $Cm^R$ | This study |
| pKU2293 | pACYC184 derived plasmid with N104-aroA$_{E.\ coli}$, $Cm^R$ | This study |
| pKU2294 | pACYC184 derived plasmid with N154-aroA$_{E.\ coli}$, $Cm^R$ | This study |
| pKU2295 | pACYC184 derived plasmid with N182-aroA$_{E.\ coli}$, $Cm^R$ | This study |
| pKU2296 | pACYC184 derived plasmid with N184-aroA$_{E.\ coli}$, $Cm^R$ | This study |
| pKU2297 | pACYC184 derived plasmid with N376-aroA$_{E.\ coli}$, $Cm^R$ | This study |
| pKU2298 | pACYC184 derived plasmid with N383-aroA$_{E.\ coli}$, $Cm^R$ | This study |
| pKU2299 | pBR322 derived plasmid with C68-aroA$_{E.\ coli}$, $Ap^R$ | This study |
| pKU2300 | pBR322 derived plasmid with C74-aroA$_{E.\ coli}$, $Ap^R$ | This study |
| pKU2301 | pBR322 derived plasmid with C86-aroA$_{E.\ coli}$, $Ap^R$ | This study |
| pKU2302 | pBR322 derived plasmid with C105-aroA$_{E.\ coli}$, $Ap^R$ | This study |
| pKU2303 | pBR322 derived plasmid with C155-aroA$_{E.\ coli}$, $Ap^R$ | This study |
| pKU2304 | pBR322 derived plasmid with C183-aroA$_{E.\ coli}$, $Ap^R$ | This study |
| pKU2305 | pBR322 derived plasmid with C185-aroA$_{E.\ coli}$, $Ap^R$ | This study |

TABLE 3-continued

Bacteria strains and plasmids used in this study

| strain/plasmid | features | Origin/Reference |
|---|---|---|
| pKU2306 | pBR322 derived plasmid with C377-aroA$_{E.\ coli}$, Ap$^R$ | This study |
| pKU2307 | pBR322 derived plasmid with C384-aroA$_{E.\ coli}$, Ap$^R$ | This study |

Ap, ampicillin;
Cm, chloromycetin;
$^R$, resistance.

3.2 Medium

See Section 1.2 of this example.

3.3 Reagent

Restriction endonuclease, T$_4$DNA ligase, DNA polymerase, and DNA marker were from Takara. All the other chemicals were reagents of analytical grade.

3.4 Genetic Manipulation

Preparation of plasmid DNA, digestion with restriction endonuclease, ligation reaction and horizontal agarose electrophoresis in Tris-boric acid-EDTA buffer were carried out according to standard procedures (Maniatis et al., 1982).

3.5 Plasmid Construction a. Construction of pBR322 Series Plasmid (Encoding C-Terminal Peptides of EPSPS)

The genes encoding C-terminal peptides of *E. coli* EPSPS were amplified taking pKU2009 (*E. coli* aroA gene) as a template. The resulting products were ligated into the NcoI and BamHI sites of pKU2100 to obtain the series plasmids encoding C-terminal peptides of EPSPS (Table 3).

b. Construction of pACYC184 Series Plasmid (Encoding N-Terminal Peptides of EPSPS)

The genes encoding N-terminal peptides of *E. coli* EPSPS were amplified taking pKU2009 or pGMO as a template. The resulting products were ligated into the EcoRV and BamHI sites of pACYC184 to obtain the series plasmids encoding N-terminal peptides of EPSPS (Table 3).

All the plasmids constructed above are confirmed of correct sequence by sequencing.

3.6 In Vivo Complementation

The pBR322 plasmids constructed in section 3.5 a and their relevant pACYC1184 plasmids constructed in section 3.5 b were introduced respectively or together into *E. coli* strain AB2829 deficient in aroA gene. Then the strains were streaked on solid M63 restrictive medium and cultured overnight to test the growth.

3.7 Results

Fragments having 21 different divisional sites were designed in total based on the structure of *E. coli* EPSPS and were investigated for EPSPS fragment complementation. For 3 of the fragment pairs, the divisional sites were located in α-helix, with the following results: neither N31/C32 nor N245/C246 complements the growth of aroA gene mutant *E. coli* strain AB2829 on the restrictive medium; complementation of N105/C106 was poor. For 3 of the fragment pairs, the divisional sites were located in β-sheet, with the following results: neither N73/C74 nor N238/C239 complements the EPSPS enzyme activity, while N224/C225 complements the growth of AB2829 on the restrictive medium. For 5 of the fragment pairs, the divisional sites were located in the joining regions between β-sheets or between α-helices. Of those 5 fragment pairs, only N165/C166 failed to complement the growth of AB2829 on the M63 restrictive medium, while the other four pairs of EPSPS fragments complement EPSPS activity. For 6 of the fragment pairs, the divisional sites were located between two folding units. Of those 6 pairs, only N234/C235 failed to complement EPSPS activity, while the other five pairs of fragments complemented well on the growth of AB2829 on the M63 restrictive medium. These results (as well as the results for four other pairs) are depicted in Table 4.

TABLE 4

Fragment complementation of *E. coli* EPSPS

| EPSPS fragment | | region where the divisional site were located | complementation condition | | |
|---|---|---|---|---|---|
| N-terminal | C-terminal | | N-terminal | C-terminal | N-terminal + C-terminal |
| N31 | C32 | α-helix | − | − | − |
| N67 | C68 | between two β-sheets | − | − | + |
| N73 | C74 | β-sheet | − | − | − |
| N85 | C86 | between folding unit 3 and 4 | − | − | +++ |
| N104 | C105 | α-helix | − | − | +/− |
| N154 | C155 | between folding unit 4 and 5 | − | − | +++ |
| N165 | C166 | between α-helix and β-sheet | − | − | − |
| N182 | C183 | between α-helix and β-sheet | − | − | + |
| N184 | C185 | between α-helix and β-sheet | − | − | ++ |
| N218 | C219 | between two β-sheets | − | − | ++ |
| N224 | C225 | β-sheet | − | − | + |
| N227 | C228 | between folding unit 3 and 5 | − | − | ++ |
| N234 | C235 | between folding unit 3 and 5 | − | − | − |
| N238 | C239 | β-sheet | − | − | − |
| N240 | C241 | between two domains | − | − | − |
| N245 | C246 | α-helix | − | − | − |
| N259 | C260 | β-sheet | − | − | + |
| N298 | C299 | between folding unit 2 and 6 | − | − | +++ |
| N371 | C372 | between folding unit 1 and 6 | − | − | +++ |

TABLE 4-continued

Fragment complementation of E. coli EPSPS

| EPSPS fragment | | region where the divisional site were located | complementation condition | | |
|---|---|---|---|---|---|
| N-terminal | C-terminal | | N-terminal | C-terminal | N-terminal + C-terminal |
| N376 | C377 | between folding unit 1 and 6 | − | − | +++ |
| N383 | C384 | between α-helix and β-sheet | − | − | + |

−, failed to grow;
+, able to grow.

Example 2

Fragment Complementation of P. putida Glyphosate-Tolerant EPSPS

Fragment complementation experiments were carried out using the glyphosate-tolerant EPSPS gene of P. putida CGMCC 0739. The plasmids, media, strains and the protocols are the same as in Example 1. The reconstituted enzyme activity was tested by growth on the medium containing 100 mM glyphosate.

TABLE 5

Fragment complementation of P. putida glyphosate-tolerant EPSPS

| EPSPS fragment | region where the divisional site locates | complementation condition |
|---|---|---|
| N208/C209 | between α-helix and β-sheet | + |
| N214/C215 | in β-sheet | + |
| N219/C220 | between folding units | ++ |
| N222/C223 | between folding units | + |
| N224/C225 | between folding units | ++ |
| N233/C234 | between two domains | − |
| N234/C234 | between two domains | − |
| N236/C237 | between two domains | − |

Primers used are listed as follows:
N-terminal forward primer.

```
ppN5':
5'-TGA GTG ACT GAA AGT GAA AGT AAC AAT ACA G-3'
```

N-terminal reversed primer is described below.
C-terminal reverse primer:

```
ppC3'(BamHI):
5'-CGG GAT CCC TTC TTC GGA CAA TGA CAG AC-3'
```

C-terminal reverse primer is described below.

```
N208/C209 +
ppN2083'(BamHI): 5'-CGG GAT CCT CAG GGA GTC TTC AAA CCA AAC C-3'
ppC2095'(NcoI):   5'-CAT GCC ATG GAG AAT CGA AAC TAT GAA G-3'

N214/C215 +
ppN2143'(BamHI): 5'-CGG GAT CCT CAT TCA TAG TTT CGA TTC TCG G-3'
ppC2155'(NcoI):   5'-CAT GCC ATG GAG TTT TAT TTC AAA GCC GG-3'

N219/C220 + +
ppN2193'(BamHI): 5'-CGG GAT CCT CAT TTG AAA TAA AAC TCT TCA TAG-3'
ppC2205'(NcoI):   5'-CAT GCC ATG GCC GGG AAT GTA TAT GAT GAA AC-3'

N222/C223 +
ppN2223'(BamHI): 5'-CGG GAT CCT CAA TTC CCG GCT TTG AAA TAA AAC-3'
ppC2235'(NcoI):   5'-CAT GCC ATG GTA TAT GAT GAA ACG AAA ATG-3'

N224/C225 + +
ppN2243'(BamHI): 5'-CGG GAT CCT CAA TAT ACA TTC CCG GCT TTG-3'
ppC2255'(NcoI):   5'-CAT GCC ATG GAT GAA ACG AAA ATG CAA CG-3'

N233/C234
ppN2333'(BamHI): 5'-CGG GAT CCT CAG GTG TAT CGT TGC ATT TTC G-3'
ppC2345'(NcoI):   5'-CAT GCC ATG GTA GAA GGC GAC TGG AGC G-3'

N234/C235
ppN2343'(BamHI): 5'-CGG GAT CCT CAT ACG GTG TAT CGT TGC ATT TTC-3'
ppC2355'(NcoI):   5'-CAT GCC ATG GAA GGC GAC TGG AGC GGT GG-3'

N236/C237
ppN2363'(BamHI): 5'-CGG GAT CCT CAG CCT TCT ACG GTG TAT CGT TG-3'
ppG2375'(NcoI):   5'-CAT GCC ATG GAC TGG AGC GGT GGT GCT TT-3'
```

The invention claimed is:

1. A method for reconstitution of an active 5-enolpyruvylshikimate-3-phosphate synthase (EPSPS) structure from at least two inactive EPSPS fragments which constitute an EPSPS fragment pair, said method comprising, providing a first inactive EPSPS fragment and a second inactive EPSPS fragment, allowing the first and the second fragments to associate to form a structure characterized in that it, exhibits EPSPS activity; lacks a covalent bond joining the fragments; and lacks complementary non-EPSPS sequences, the fragment pair being selected from a group of *E. coli* EPSPS fragment pairs consisting of the following: N67/C68, N85/C86, N104/C105, N154/C155, N182/C183, N184/C185, N218/C219, N224/C225, N227/C228, N259/C260, N298/C299, N371/C372, N376/C377, N383/C384, or is selected from a group of *P. putida* CGMCC 0739 EPSPS fragment pairs consisting of the following: N208/C209, N214/C215, N219/C220, N222/C223, N224/C225.

* * * * *